US012616376B2

(12) United States Patent
Oh

(10) Patent No.: US 12,616,376 B2
(45) Date of Patent: May 5, 2026

(54) APPARATUS FOR INPUTTING COMBINED IMAGE OF PHOTOACOUSTIC IMAGE AND ULTRASONIC IMAGE AND METHOD THEREOF

(71) Applicant: PUKYONG NATIONAL UNIVERSITY INDUSTRY-UNIVERSITY COOPERATION FOUNDATION, Busan (KR)

(72) Inventor: Jung Hwan Oh, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 226 days.

(21) Appl. No.: 18/225,243

(22) Filed: Jul. 24, 2023

(65) Prior Publication Data

US 2024/0156354 A1     May 16, 2024

(30) Foreign Application Priority Data

Nov. 14, 2022     (KR) ........................ 10-2022-0151226

(51) Int. Cl.
*A61B 5/00*          (2006.01)
*G06T 5/50*          (2006.01)

(52) U.S. Cl.
CPC .......... *A61B 5/0095* (2013.01); *A61B 5/0035* (2013.01); *G06T 5/50* (2013.01);
(Continued)

(58) Field of Classification Search
CPC .................................................. A61B 5/0095
See application file for complete search history.

(56) References Cited

U.S. PATENT DOCUMENTS 10,354,379 B2 *   7/2019   Zalev ................... A61B 5/0095
2011/0088477 A1 *   4/2011   Someda ............... A61B 5/0035
                                                            73/632
(Continued)

FOREIGN PATENT DOCUMENTS

JP          2013-017760 A      1/2013
JP          2018-011950 A      1/2018
(Continued)

OTHER PUBLICATIONS

Sensors 2020, 20, 3714; Article; In Vivo Dual-Modal Photoacoustic and Ultrasound Imaging of Sentinel Lymph Nodes Using a Solid-State Dye Laser System; Moongyu Han et al.; Jul. 2, 2020.

*Primary Examiner* — Rajeev P Siripurapu
(74) *Attorney, Agent, or Firm* — Han's Law Office

(57)          ABSTRACT

Disclosed is an apparatus for inputting a combined photoacoustic/ultrasonic image, which generates 3D image information for a object by performing 2D scanning on the object by a first linear motion of a photoacoustic probe and an ultrasonic probe, and a second linear motion perpendicular to the first linear motion, the apparatus comprising: a transfer unit that move the photoacoustic probe and the ultrasonic probe with respect to the object in the first and/or second direction; a photoacoustic unit that outputs a laser to the object, receives a first ultrasound from the object by the laser, and generates a photoacoustic image signal; an ultrasonic unit that outputs an ultrasound to the object, receives a second ultrasound from the object by the ultrasound, and generates an ultrasonic image signal; and a main controller that combines photoacoustic image and ultrasonic image to generate a combined photoacoustic/ultrasonic image.

17 Claims, 8 Drawing Sheets

(52) U.S. Cl.
CPC ............... *G06T 2207/10136* (2013.01); *G06T 2207/20221* (2013.01)

(56)                        References Cited

U.S. PATENT DOCUMENTS

| | | | | |
|---|---|---|---|---|
| 2013/0039147 A1* | 2/2013 | Witte | .................... | G01S 15/02 |
| | | | | 367/7 |
| 2014/0024918 A1* | 1/2014 | Hirota | .................. | A61B 5/7425 |
| | | | | 600/407 |
| 2016/0135688 A1* | 5/2016 | Ebisawa | .............. | A61B 8/0825 |
| | | | | 600/407 |

FOREIGN PATENT DOCUMENTS

| | | | |
|---|---|---|---|
| KR | 10-1749602 | B1 | 6/2017 |
| KR | 10-1949404 | B1 | 2/2019 |
| KR | 10-1952921 | B1 | 2/2019 |
| KR | 10-2036058 | B1 | 10/2019 |
| KR | 10-2301418 | B1 | 9/2021 |
| WO | 2011/101492 | A2 | 8/2011 |

\* cited by examiner

APPARATUS FOR INPUTTING COMBINED IMAGE OF PHOTOACOUSTIC IMAGE AND ULTRASONIC IMAGE AND METHOD THEREOF

CROSS-REFERENCE TO RELATED APPLICATION

This application claims priority to and the benefit of Korean Patent Application No. 10-2022-0151226 filed on Nov. 14, 2022, in the Korean Intellectual Property Office, the entire disclosure of which is incorporated herein by reference.

BACKGROUND

1. Field

The present disclosure relates to an apparatus for inputting a combined photoacoustic/ultrasonic image and a method thereof. More specifically, the present disclosure relates to an apparatus for inputting a combined photoacoustic/ultrasonic image and a method thereof, in which a combined photoacoustic/ultrasonic image in which photoacoustic and ultrasonic images for the inside of a to-be-examined object (subject) are combined can be generated, while integrally moving a photoacoustic probe and an ultrasonic probe at high speed.

2. Description of the Related Art

When light having very high energy is irradiated to a to-be-examined object, the to-be-examined object that absorbs the light energy thermally expands elastically. Due to this elastic expansion, a pressure wave is generated, and the generated pressure wave takes the form of an ultrasonic wave. This phenomenon is called a "photo-acoustic effect", and an ultrasonic signal generated by this expansion is called a photoacoustic signal.

Recently, a technique for acquiring state information of an object, particularly the inside of the to-be-examined object, by using a photoacoustic effect, and generating the same as image information, has been spotlighted. Particularly in the medical field, a lot of research on this is being done. In the medical field, during a disease treatment process, it is often necessary to visually check state information about the inside of a living body. Currently, tools that are widely used as a method for generating image information about the inside of a living body include X-ray, CT, MRI, etc., as is well known. However, it has been reported that these methods are accompanied by various problems, including expensive equipment, an extremely low resolution of a generated image, a narrow field of view (FOV), an extended time required to implement the image, or possibility of harming the human body due to continuous use.

A method for generating a photoacoustic image of an internal state of a living body by using a photoacoustic effect is attracting attention as an alternative to these methods. In particular, the photoacoustic image can show blood vessel-related information concerning the inside of the human body, and thus can be an important technology in the medical field.

Meanwhile, an ultrasonic system may generate an ultrasonic image by outputting an ultrasonic signal to a to-be-examined object and receiving an ultrasonic signal output from the to-be-examined object. In particular, the ultrasonic system has non-invasive and non-destructive properties for an object, and is widely used in various fields. Recently, an ultrasonic system is used to generate a 2D or 3D image of the internal shape of an object. In particular, ultrasonic images can show information related to the structure of a human body.

A photoacoustic image can mainly show only blood vessel-related information, and an ultrasonic image can mainly show only structure-related information. Accordingly, there is a need for a technology capable of simultaneously displaying structure-related information and blood vessel-related information for the inside of a human body.

SUMMARY

The present disclosure provides an apparatus for inputting a combined photoacoustic/ultrasonic image and a method thereof, in which a combined photoacoustic/ultrasonic image in which the photoacoustic and ultrasonic images for the outside and/or the inside of a to-be-examined object are combined can be generated, while integrally moving a photoacoustic probe and an ultrasonic probe at high speed.

Provided is an apparatus for inputting a combined photoacoustic/ultrasonic image, according to an embodiment of the present disclosure, which generates three-dimensional (3D) image information for a to-be-examined object by performing two-dimensional (2D) scanning on the to-be-examined object by first-direction linear motions of a photoacoustic probe and an ultrasonic probe and a second-direction linear motion that is substantially perpendicular to the first-direction linear motion, the apparatus comprising: a transfer unit that linearly relatively move the photoacoustic probe and the ultrasonic probe with respect to the to-be-examined object in the first direction and/or the second direction; a photoacoustic input unit that outputs a laser pulse output to the to-be-examined object, receives a first ultrasound input from the to-be-examined object by the laser pulse output, and generates a photoacoustic image signal; an ultrasonic input unit that outputs an ultrasonic output to the to-be-examined object, receives a second ultrasonic input from the to-be-examined object by the ultrasonic output, and generates an ultrasonic image signal; an analog/digital (A/D) converter that receives the photoacoustic image signal and the ultrasonic image signal and converts each into a digital image signal; and a main controller that receives the digital image signal, generates photoacoustic image information and ultrasonic image information for the to-be-examined object, and combines the photoacoustic image information and ultrasonic image information to generate a combined photoacoustic/ultrasonic image, wherein a first position at which the laser pulse output is focused and a second position at which the ultrasonic output is focused are spaced apart by a set separation distance.

At the same time point or within the same data input period, the laser pulse output and the ultrasonic output may be point-focused at different positions of the to-be-examined object.

The photoacoustic input unit may include a laser probe that outputs the laser pulse output to the to-be-examined object and a first ultrasonic probe that receives the first ultrasonic input, and the ultrasonic input unit may include a second ultrasonic probe that outputs the ultrasonic output to the to-be-examined object and receives the second ultrasonic input.

The laser probe and the first ultrasonic probe may be arranged to be staggered at an angle greater than 45 degrees, and the second ultrasonic probe may be arranged to be staggered at an angle less than 45 degrees or substantially parallel to either one of the laser probe and the first ultrasonic probe.

The laser probe, the first ultrasonic probe, and the second ultrasonic probe may be installed in one housing and transferred together.

The first position and the second position may be spaced apart from each other in the first direction or the second direction.

With respect to the set laser and ultrasonic output conditions or input conditions, the separation distance may be set in advance by extracting the best image quality of the photoacoustic image and the ultrasound image or the shortest distance without image quality degradation from a plurality of pieces of photoacoustic image information and ultrasonic image information input while varying the separation distance.

The separation distance may be set in real time as the shortest distance by determining the quality of the photoacoustic image and the ultrasound image from the input photoacoustic image information and the ultrasonic image information.

The separation distance may be controlled by moving the second ultrasonic probe that receives the second ultrasonic input in parallel or rotating about a reference axis.

The photoacoustic image information or the ultrasonic image information may be shifted by the separation distance and combined.

The ultrasonic input unit may include an ultrasonic transceiving unit that generates an ultrasonic output signal (output channel) for generating the ultrasonic output, receives the first ultrasonic input and the second ultrasonic input, and generates a photoacoustic image signal and an ultrasonic image signal, respectively, the ultrasonic transceiving unit includes a first input channel and a second input channel, the photoacoustic image signal may be generated by inputting the first ultrasound input to the first input channel, and the ultrasound image signal may be generated by inputting the second ultrasound input to the second input channel.

The apparatus may include: a pulse signal generator that generates and outputs a reference pulse signal at a set interval; a first linear encoder that generates linear motion information of the photoacoustic probe in the first direction; a laser generator that outputs a laser pulse at a set interval to the to-be-examined object according to the reference pulse signal and the linear motion information in the first direction; and a trigger controller that generates an output trigger signal at a set interval according to the reference pulse signal and the linear motion information in the first direction.

The ultrasonic transceiving unit may generate the photoacoustic image signal and the ultrasonic image signal corresponding to the linear motion information in the first direction, respectively, according to the output trigger signal.

The second ultrasonic probe may output an ultrasonic output corresponding to an output trigger signal generated by a trigger controller and receive the ultrasonic input corresponding to the linear motion information in the first direction according to the output trigger signal.

In the main controller, photoacoustic image information for the to-be-examined object may be generated by sequentially combining the photoacoustic digital image signal with the photoacoustic image information corresponding to each trigger pulse of the output trigger signal in the positive or negative direction of the first direction in units of scan lines, and ultrasonic image information for the to-be-examined object may be generated by sequentially combining the ultrasonic digital image signal with the ultrasonic image information corresponding to each trigger pulse of the output trigger signal in the positive or negative direction of the first direction in units of scan lines.

The laser pulse output and the ultrasonic output may be simultaneously output.

The reference pulse signal may be output to the trigger controller and the laser generator.

3D image information for the to-be-examined object may be generated by the one-time 2D scanning of the housing, and, within each scanning line, the first ultrasonic input and the second ultrasonic input may be alternately performed.

In the method for inputting a combined photoacoustic/ultrasonic image, according to an embodiment of the present disclosure, the combined photoacoustic/ultrasonic image may be acquired by using the combined photoacoustic/ultrasonic image input apparatus 1 by the above-described method.

DETAILED DESCRIPTION

Figure 1:
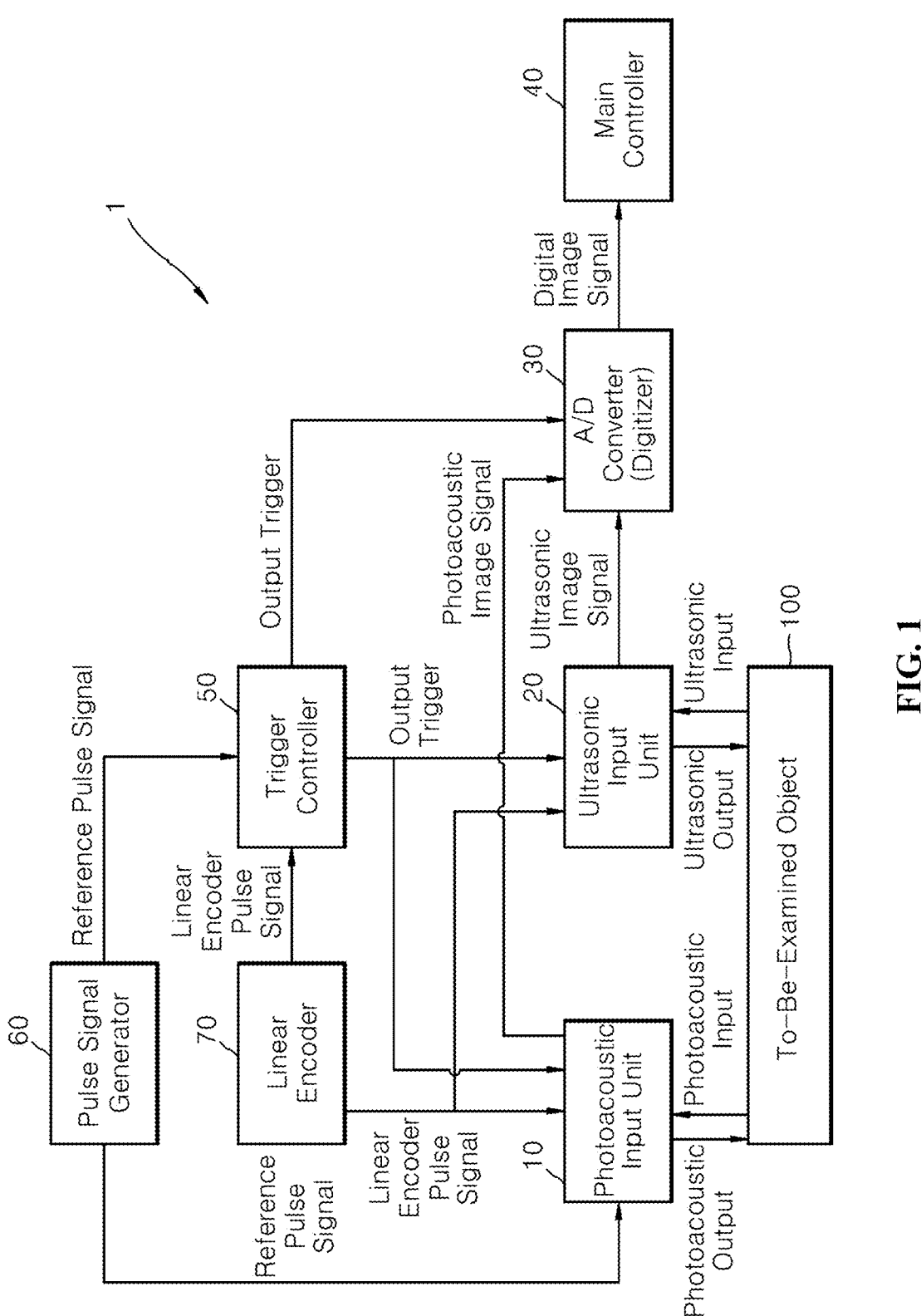
FIG. 1 is a block diagram schematically showing a combined photoacoustic/ultrasonic image input apparatus according to an embodiment of the present disclosure.

Hereinafter, specific details for implementing the present disclosure will be described in detail with reference to the accompanying drawings based on preferred embodiments of the present disclosure. Here, as disclosed in the drawing of one embodiment, the same reference numerals are assigned to the same components as those disclosed in the drawings of another embodiment, and descriptions in other embodiments may be equally applied, and detailed description thereof is simplified or omitted here. In addition, known functions or configurations related to the present disclosure refer to known technologies, and detailed description thereof is simplified or omitted here.

In addition, although the terms used in this specification are selected from generally known and used terms, the terms used herein may be varied depending on operator's intention or customs in the art, advent of new technology, or the like. In addition, in a specific case, some of the terms mentioned in the description of the present disclosure have been arbitrarily selected by the inventor(s), and, in this case, the detailed meanings of the terms will be described in detail in relevant parts of the description of the present disclosure. Therefore, the terms used in this specification should be defined based on the meanings of the terms and the overall content of the present disclosure, not simply on the basis of actual terms used.

Throughout the specification, it will be understood that the term "comprising" specifies the addition and/or presence of one or more other components, but does not preclude the possibility of excluding the stated components features, unless the context clearly indicates otherwise. In addition, the term "unit" used herein refers to software or a hardware element such as a field-programmable gate array (FPGA), an application specific integrated circuit (ASIC), etc. However, the meaning of "unit" is not limited to software or hardware. The "unit" may advantageously be configured to reside on the addressable storage medium and configured to drive one or more processors. Thus, a unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and "unit(s)" may be combined into fewer components and "unit(s)" or further separated into additional components and "unit(s)".

A method for generating a photoacoustic image of an object, for example, the inside of a living body by using a photoacoustic effect will now be described. First, an optical beam (e.g., a laser beam) is irradiated to a specific part of a living body, from which a 3D image is intended to acquire, a photoacoustic signal generated according to thermal elastic expansion generated in the specific part by the irradiated beam (an ultrasonic signal) is acquired through an ultrasonic probe (ultrasonic transducer), and the acquired photoacoustic signal is subjected to predetermined signal processing to generate 3D photoacoustic image information for the inside of the living body.

In addition, a method for generating an ultrasonic image for the inside of a to-be-examined object will now be described. First, an ultrasonic beam is irradiated to a specific part of a living body, from which a 3D image is intended to acquire, an ultrasonic signal generated in the specific part by the irradiated ultrasonic beam is acquired through an ultrasonic probe (ultrasonic transducer), and the acquired ultrasonic signal is subjected to predetermined signal processing to generate 3D ultrasonic image information for the inside of the living body.

A high-speed scanning photoacoustic image input apparatus according to an embodiment of the present disclosure may include a photoacoustic microscope (PAM). In addition, a photoacoustic probe for a photoacoustic microscope (PAM) may scan a target area including a to-be-examined object while moving at high speed by using a slider crank mechanism. The high-speed scanning photoacoustic image acquiring apparatus may convert a unidirectional rotational motion of a driving motor into a linear reciprocating motion of the photoacoustic probe connected to the driving motor. In addition, a three-dimensional (3D) image of the to-be-examined object may be generated by two-dimensional (2D)

scanning of the to-be-examined object by the linear motion of the photoacoustic probe and the vertical motion perpendicular to the linear motion.

In the photoacoustic microscope (PAM) of the present disclosure, an optical-resolution PAM (OR-PAM) having micron-scale spatial resolution by focusing an optical beam (e.g., a laser beam) may be used. The optical-resolution PAM (OR-PAM) may use a tight optical focus. Meanwhile, the acoustic-resolution PAM (AR-PAM) may use an acoustic focus.

Since the optical-resolution PAM (OR-PAM) relies on an optical beam that is much tighter than an acoustic beam, there is an advantage in that high-resolution images can be acquired, compared to an acoustic-resolution PAM (AR-PAM). In addition, the optical-resolution PAM (OR-PAM) has rich optical absorption contrast, and thus can be a powerful imaging tool in most fields related to medicine, including many fields such as biology, dermatology, neurology, oncology, ophthalmology, pathology, and so on.

To achieve maximization of a signal-to-noise ratio (SNR) and optimization of spatial resolution, the optical-resolution PAM (OR-PAM) may apply confocal and coaxial configurations of optical excitation beams and acoustic detection beams. Volumetric imaging is typically achieved by point-by-point raster scanning of optical and acoustic beams, for which a stepping motor scanning stage may be applied. Volumetric imaging is typically achieved by point-by-point raster scanning of optical and acoustic beams, and, to this end, stepping motor scanning stage may be applied.

Because of the scanning step size required by micron-level lateral resolution, the scanning speed (and consequent imaging speed) and scanning range of the optical-resolution PAM (OR-PAM) may be low (B-scan rate of approximately 1 Hz in a scanning range of 1 mm). Due to such a low imaging speed, it has not been easy to acquire tissue's dynamic information such as transient drug response or skin vasculature by an optical-resolution PAM (OR-PAM).

Meanwhile, in the optical-resolution PAM (OR-PAM), there may be various methods for improving the field of view (FOV) corresponding to a scanning range, increasing the scanning speed or shortening the scanning time, and maintaining a high signal-to-noise ratio (SNR). In order to implement an optical-resolution PAM (OR-PAM), trade-offs of these three characteristics are required, and these trade-offs may act as a factor that makes it difficult to implement the optical-resolution PAM (OR-PAM) that satisfies all three characteristics. This is because a required scanning time depends on a pulse repetition rate of laser and a scanning mechanism, and is limited by the sound speed of a photoacoustic (PA) wave in a tissue.

Figure 2:
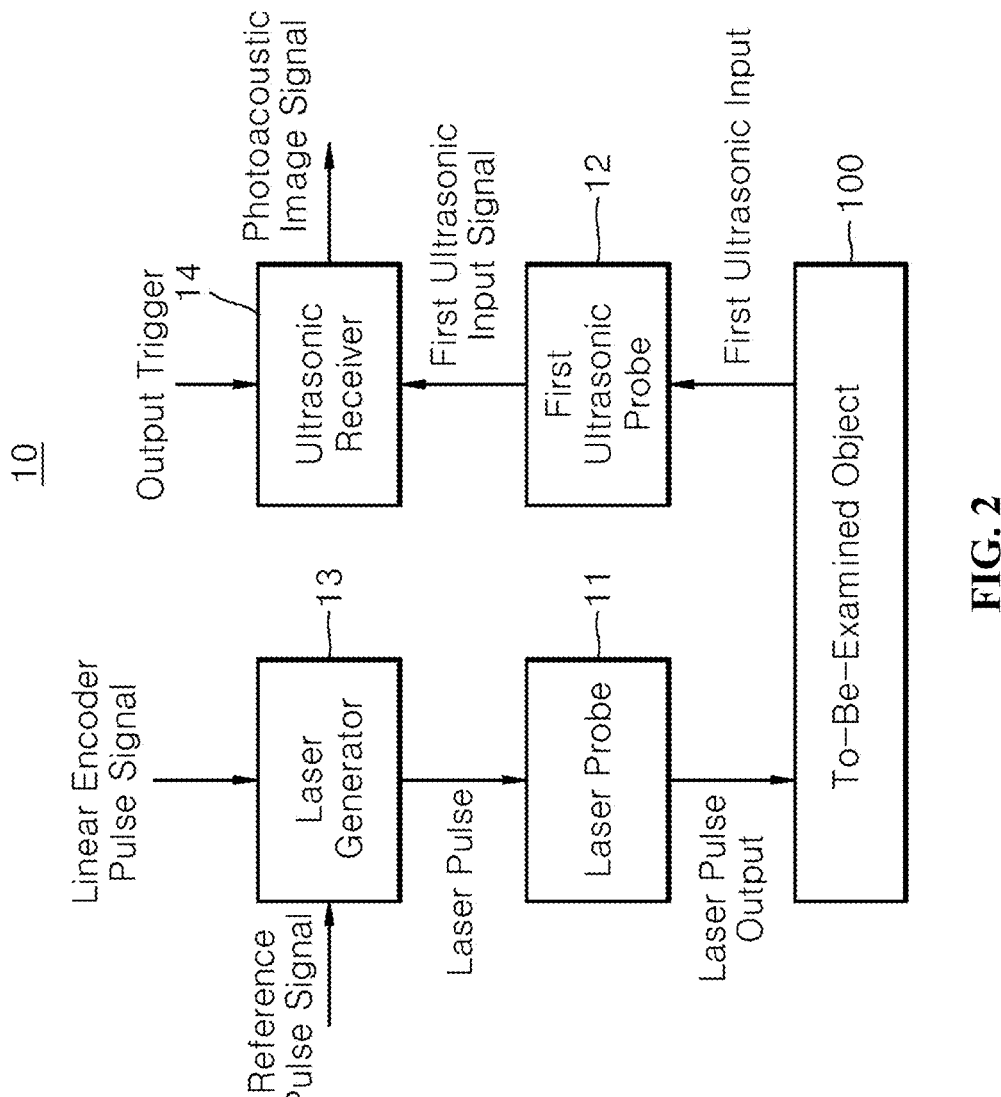
FIG. 2 is a block diagram schematically showing a photoacoustic input unit in the combined photoacoustic/ultrasonic image input apparatus of FIG. 1.
Figure 3:
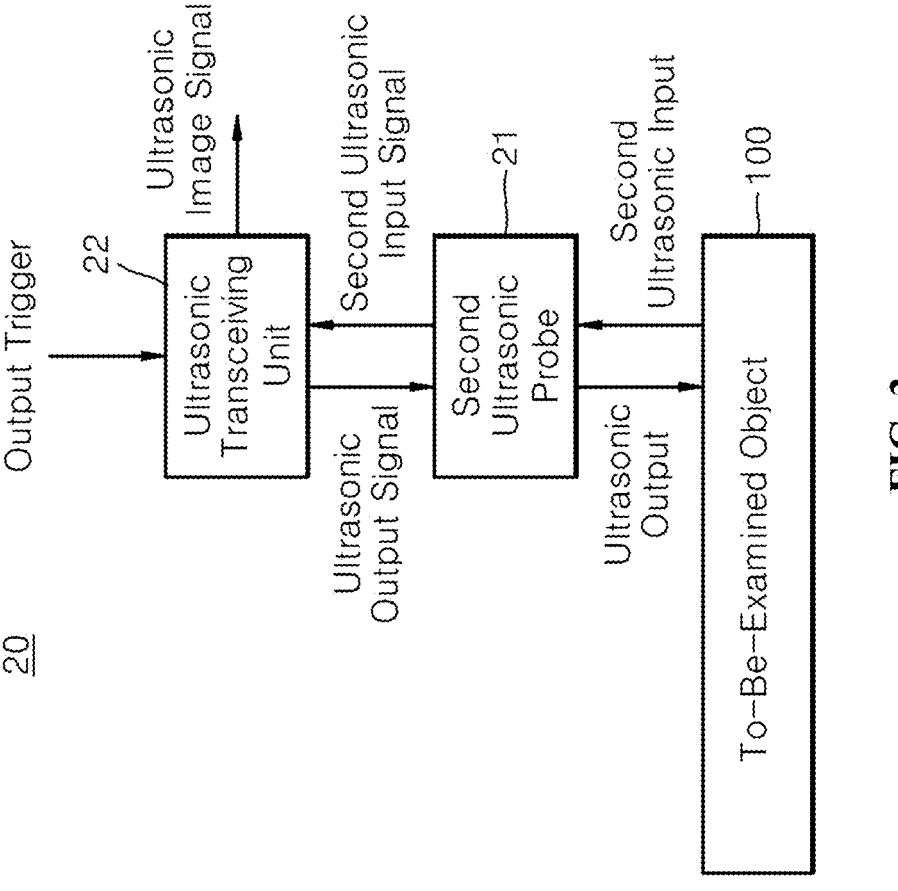
FIG. 3 is a block diagram schematically showing an ultrasonic input unit in the combined photoacoustic/ultrasonic image input apparatus of FIG. 1.
Figure 4:
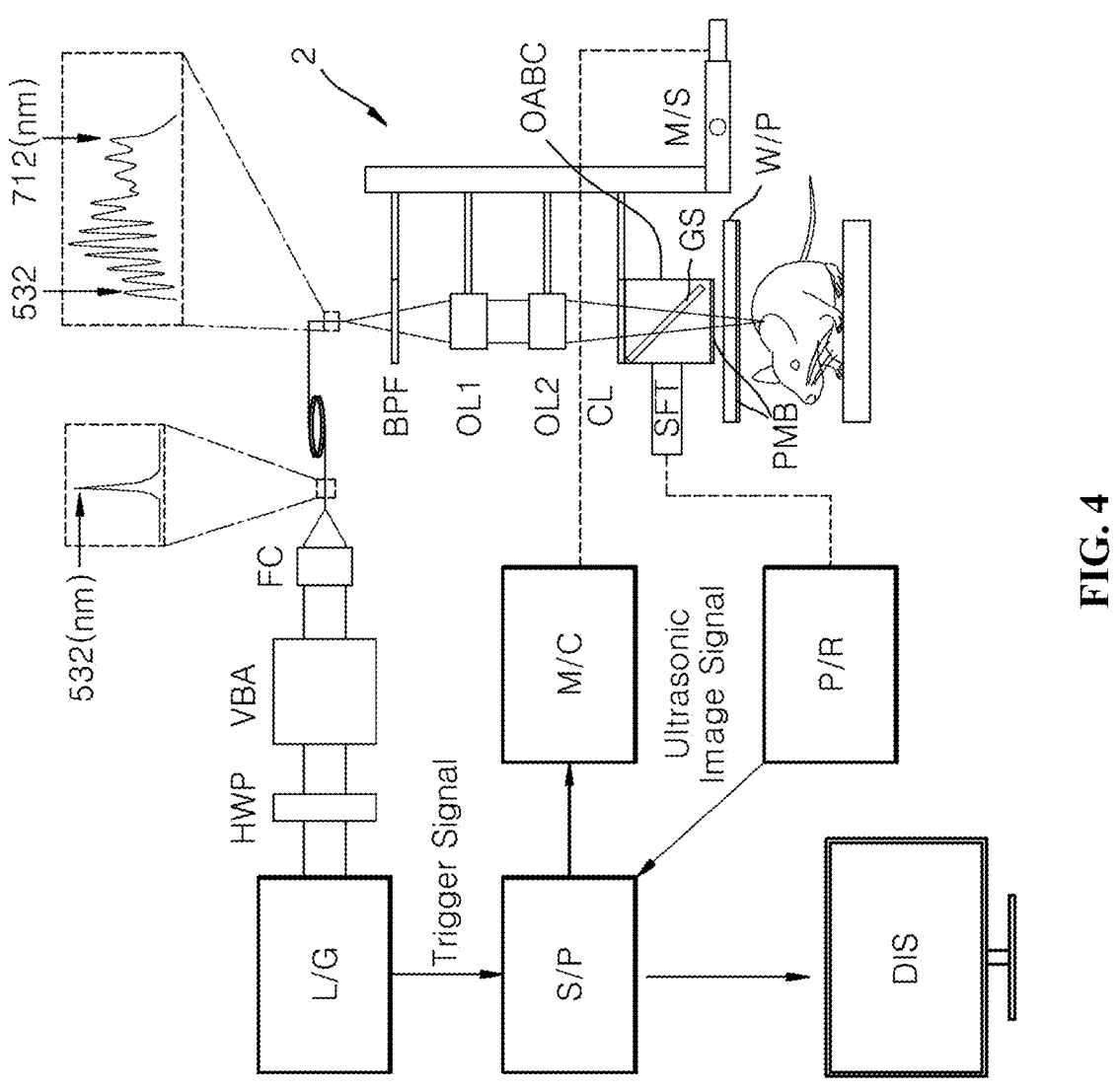
FIG. 4 is a conceptual diagram schematically showing an optical-resolution type combined photoacoustic/ultrasonic image input apparatus of an according to another embodiment of the present disclosure.

FIG. 1 schematically shows a block diagram of a combined photoacoustic/ultrasonic image input apparatus 1 according to an embodiment of the present disclosure. FIG. 2 schematically shows a block diagram of a photoacoustic input unit 20 in the combined photoacoustic/ultrasonic image input apparatus 1 of FIG. 1. FIG. 3 schematically shows a block diagram of an ultrasonic input unit 20 in the combined photoacoustic/ultrasonic image input apparatus 1 of FIG. 1. FIG. 4 is a conceptual diagram schematically showing an optical-resolution type combined photoacoustic/ultrasonic image input apparatus of an according to another embodiment of the present disclosure.

Figure 5:
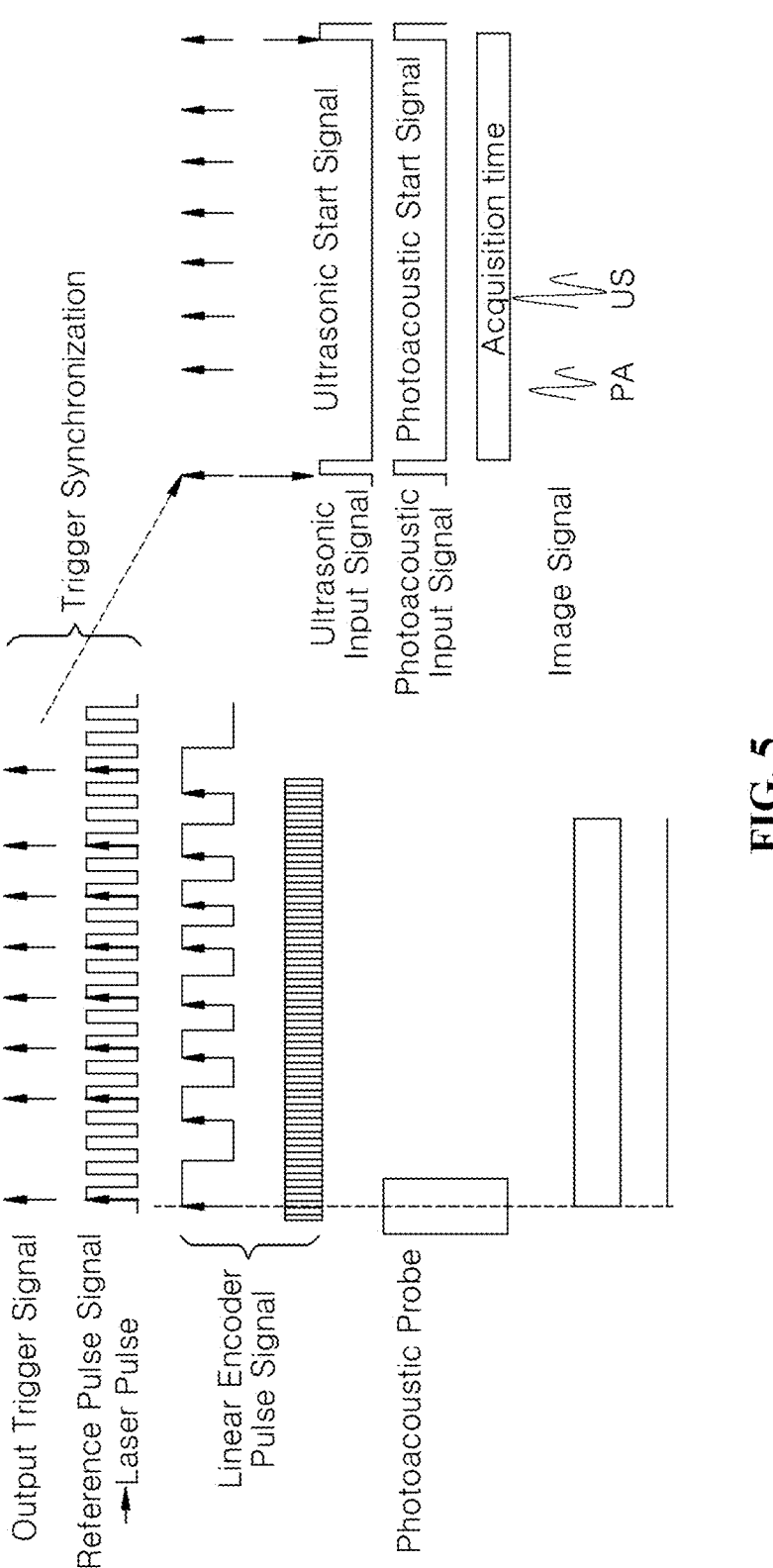
FIG. 5 is a timing diagram schematically showing a method for generating a combined image by a photoacoustic image signal in the combined photoacoustic/ultrasonic image input apparatus of FIG. 1.

FIG. 5 schematically shows a timing diagram of a method for generating a combined image by a photoacoustic image signal in the combined photoacoustic/ultrasonic image input apparatus of FIG. 1.

Figure 6:
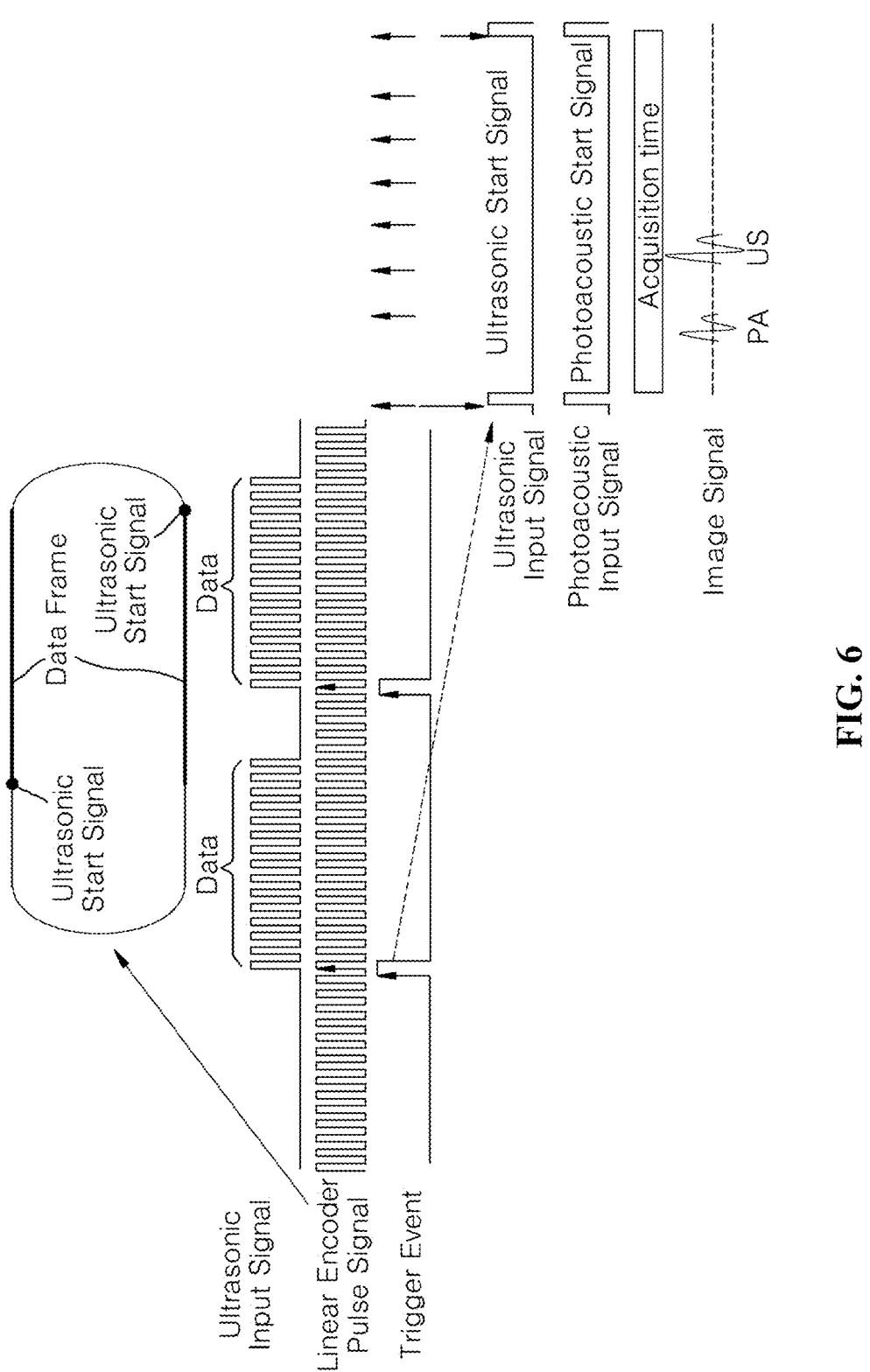
FIG. 6 is a timing diagram schematically showing a method for generating a combined image by an ultrasound image signal in the combined photoacoustic/ultrasonic image input apparatus of FIG. 1.

FIG. 6 schematically shows a timing diagram of a method for generating a combined image by an ultrasound image signal in the combined photoacoustic/ultrasonic image input apparatus of FIG. 1.

Referring to the drawings, the combined photoacoustic/ultrasonic image input apparatus 1 may generate a 3D combined photoacoustic/ultrasonic image for a to-be-examined object, by integrally performing 2D scanning on the to-be-examined object by a first-direction linear motion and a second-direction linear motion that is substantially perpendicular to the first-direction linear motion by using photoacoustic probes 11, 12 and ultrasonic probe 21.

According to the present disclosure, the combined photoacoustic/ultrasonic image input apparatus 1 may generate a photoacoustic image and an ultrasonic image for the inside and/or outside of the to-be-examined object, respectively, and combine the same, while integrally moving the photoacoustic probe and the ultrasonic probe at high speed, thereby generating a combined photoacoustic/ultrasonic image by one-time 2D scanning within a short period of time.

The combined photoacoustic/ultrasonic image input apparatus 1 includes a photoacoustic probe and an ultrasonic probe, respectively, and acquires photoacoustic and ultrasonic images at different points of the to-be-examined object, respectively, and thus, the photoacoustic image and the ultrasonic image may be received without interference between photoacoustic and ultrasonic input signals. Therefore, the combined photoacoustic/ultrasonic image input apparatus 1 can quickly receive a photoacoustic image and an ultrasonic image through one-time 2D scanning.

Here, the photoacoustic probe may include a laser probe 11 that outputs a laser output to the to-be-examined object 100, and a first ultrasonic probe 12 that receives a first ultrasonic input produced from the to-be-examined object 100 by the laser output of the laser probe 11. In addition, the ultrasonic probe may include a second ultrasonic probe 21 that outputs an ultrasonic output to the to-be-examined object 100, and receives the second ultrasonic input produced from the to-be-examined object 100 by the ultrasonic output to generate an ultrasonic image signal.

The combined photoacoustic/ultrasonic image input apparatus 1, may include: a transfer unit; photoacoustic input unit 10; ultrasonic input unit 20; analog/digital (A/D) converter 30; and a main controller 40.

The transfer unit may linearly relatively move the photoacoustic probe and the ultrasonic probe with respect to the to-be-examined object 100 in the first direction and/or the second direction. The transfer unit may be implemented to integrally move the photoacoustic probe and the ultrasonic probe or to move the stage on which the object is fixed.

The photoacoustic input unit 10 may output a laser pulse output to the to-be-examined object 100, and, by the laser pulse output, may receive a first ultrasonic input corresponding to the photoacoustic input produced from the to-be-examined object 100, to generate a photoacoustic image signal. Here, the laser pulse output may be a photoacoustic output, and the first ultrasonic input may be a photoacoustic input.

The ultrasonic input unit 20 may output an ultrasonic output to the to-be-examined object 100, may receive a second ultrasonic input from the to-be-examined object 100 by the ultrasonic output, to generate an ultrasonic image signal. The A/D converter 30 may receive a photoacoustic image signal and an ultrasonic image signal and convert the same into digital image signals, respectively. Here, the digital image signals may include a digital photoacoustic image and a digital ultrasonic image signal.

The main controller 40 may receive the digital image signals to generate photoacoustic image information and ultrasonic image information of the to-be-examined object 100, and may combine the photoacoustic image information and the ultrasonic image information to generate a combined photoacoustic/ultrasonic image.

A first position at which the laser pulse output is focused on the to-be-examined object 100 and a second position at which the ultrasonic output is focused may be separated by a set separation distance. Here, each of the laser pulse output and the ultrasonic output is point-focused to improve the resolution at the time of inputting an image once.

Therefore, in the combined photoacoustic/ultrasonic image input apparatus 1, the first position at which the laser pulse output is focused and the second position at which the ultrasonic output is focused are spaced apart, and thus, a combined image without interference between the photoacoustic image and the ultrasonic image can be acquired while acquiring a combined photoacoustic/ultrasonic image in a short time by one-time 2D scanning.

The transfer unit may include a motion controller and a transfer stage, as shown in FIG. 4. Here, the transfer stage may install a photoacoustic probe and an ultrasonic probe inside the housing 201 of FIG. 7 and linearly move the housing 201 in a first direction and/or a second direction.

In addition, the transfer unit, by including a linear encoder 70 capable of measuring the linear movement amounts of the photoacoustic probe and the ultrasonic probe, may measure the linear motion amounts of the photoacoustic probe and the ultrasonic probe in first and second directions, respectively. To this end, the linear encoder 70 may include a first linear encoder that generates the first-direction linear motion information of the photoacoustic probe and the ultrasonic probe and a second linear encoder that generates the second-direction linear motion information of the photoacoustic probe and the ultrasonic probe.

As shown in FIG. 2, the photoacoustic input unit 10 may include a laser generator 13 that generates laser output, a laser probe 11 that outputs laser output to a to-be-examined object, a first ultrasonic probe 12 that receives a first ultrasonic input generated from the to-be-examined object, and an ultrasonic receiver 14 that receives the first ultrasonic input and generates a photoacoustic image signal. Here, the laser output may be a laser pulse output.

As shown in FIG. 3, the ultrasonic input unit 20 may include a second ultrasonic probe 21 that outputs an ultrasonic output to the to-be-examined object 100 and receives a second ultrasonic input, and an ultrasonic transceiving unit 22 that generates an ultrasonic output signal for generating an ultrasonic output and generates an ultrasonic image signal by receiving a second ultrasonic input.

Here, the ultrasonic transceiving unit 22 may include a first input channel, a second input channel, and a first output channel. A photoacoustic image signal may be generated by inputting a first ultrasonic input to the first input channel, and an ultrasonic image signal may be generated by inputting a second ultrasonic input to the second input channel. In this case, the ultrasonic transceiving unit 22 may include the ultrasonic receiver 14 of the photoacoustic input unit 10. In addition, the ultrasonic output generated from the ultrasonic transceiving unit 22 may be output through the first output channel. Here, the ultrasonic input may be an ultrasonic pulse input. The ultrasonic output may be an ultrasonic pulse output.

The ultrasonic transceiving unit 22 may generate an ultrasonic output signal for generating an ultrasonic output, receive the first ultrasonic input and the second ultrasonic input, respectively, to generate a photoacoustic image signal and an ultrasonic image, respectively. Here, the photoacoustic image signal may be generated from the first ultrasonic input, and the ultrasonic image signal may be generated from the second ultrasonic input. The ultrasonic transceiving unit 22 may include a pulser/receiver that generates and outputs ultrasonic pulses through the ultrasonic probe 21 and receives an ultrasonic signal reflected from the to-be-examined object through the ultrasonic probe 21, and may further include an amplifier that amplifies the input ultrasonic signal.

The A/D converter 30 may receive the photoacoustic image signal and the ultrasonic image signal from the ultrasonic transceiver 20 and convert the same into digital image signals, respectively. Here, the digital image signals may include a digital photoacoustic image in which an analog photoacoustic image signal is digitally converted and a digital ultrasonic image signal in which an analog ultrasonic image signal is digitally converted.

The main controller 40 may receive the digital photoacoustic image signal and the digital ultrasonic image signal from the A/D converter 30, respectively, to generate photoacoustic image information and ultrasonic image information of the to-be-examined object, and may combine the photoacoustic image information and the ultrasonic image information to generate a combined photoacoustic/ultrasonic image. Here, each of the digitally converted photoacoustic image information and ultrasonic image information may include location information of the to-be-examined object and digital image information corresponding to the location information.

Therefore, photoacoustic image information and ultrasonic image information corresponding to each location information may be generated in the to-be-examined object and may be combined to generate a combined photoacoustic/ultrasonic image corresponding to each location information. The main controller 40 may simultaneously display the photoacoustic image and the ultrasonic image of the to-be-examined object on one display (e.g., a monitor).

In this case, a user can check the photoacoustic image and the ultrasonic image of the to-be-examined object at once through a monitor. Accordingly, the apparatus 1 for inputting a combined photoacoustic/ultrasonic image can simultaneously display structure-related information and blood vessel-related information for the inside of a human body through the combined photoacoustic/ultrasonic image. That is, the user can check information related to blood vessels through the photoacoustic image on one screen and at the same time check information related to a structure through the ultrasonic image.

The ultrasonic transceiving unit 22 may include a pulser that generates and outputs an ultrasonic pulse through the ultrasonic probe 21 and a receiver that receives an ultrasonic signal generated from the to-be-examined object through the ultrasonic probe 21. That is, since ultrasonic transceiving unit 22 includes a an ultrasonic pulser capable of outputting an ultrasonic pulse, unlike in conventional photoacoustic input devices, a separate ultrasonic pulse can be output to the to-be-examined object through the ultrasonic probe 21.

In addition, the ultrasonic input received from the to-be-examined object may be the first ultrasonic input generated in the to-be-examined object by the laser pulse output or the second ultrasonic input generated in the to-be-examined object by the ultrasonic pulse output.

That is, in the combined photoacoustic/ultrasonic image input apparatus 1, according to an embodiment of the present disclosure, unlike conventional photoacoustic probes in which an ultrasonic signal output is received from a to-be-examined object and transmitted to the ultrasonic receiver, the ultrasonic probe 21 included in the photoacoustic probes 11 and 21 may output to the to-be-examined object the ultrasonic output according to the ultrasonic output signal generated by the ultrasonic transceiving unit 22.

Therefore, the ultrasonic probe 21 according to an embodiment of the present disclosure may generate a photoacoustic image by receiving the ultrasonic signal generated in the to-be-examined object according to the laser pulse output through the ultrasonic transceiving unit 22, and may output the ultrasonic output according to the ultrasonic output signal generated by the ultrasonic transceiving unit 22 to the to-be-examined object, and thus may generate an ultrasonic image by receiving the ultrasonic signal generated in the to-be-examined object through the ultrasonic transceiving unit 22.

Here, in the combined photoacoustic/ultrasonic image input apparatus 1, according to an embodiment of the present disclosure, a first position at which the photoacoustic image signal is received and a second position at which the ultrasonic image signal is received may be different. That is, at the same time point or within the same data input period, the laser pulse output and the ultrasonic output may be point-focused at different positions of the to-be-examined object.

In this case, by making the first position and the second position different without distinguishing between the output timing of the laser pulse output and the output timing of the ultrasonic pulse output, signal interference between the first ultrasonic input and the second ultrasonic input may be prevented.

That is, in the combined photoacoustic/ultrasonic image input apparatus 1, it is not necessary for the ultrasonic probe 21 to receive the first ultrasonic input and the second ultrasonic input by distinguishing the input timing at which the ultrasonic signal (the first ultrasonic input) generated from the to-be-examined object according to the laser pulse output is received from the input timing at which the ultrasonic signal (the second ultrasonic input) generated from the to-be-examined object according to the ultrasonic pulse output is received.

Therefore, a photoacoustic image and an ultrasonic image can be input at the same time, and the input time of the combined image may be shortened. In particular, like in the combined photoacoustic/ultrasonic image input apparatus 1, even when scanning while moving the photoacoustic probe and ultrasonic probe at high speed, images can be received without deterioration in resolution.

Figure 7:
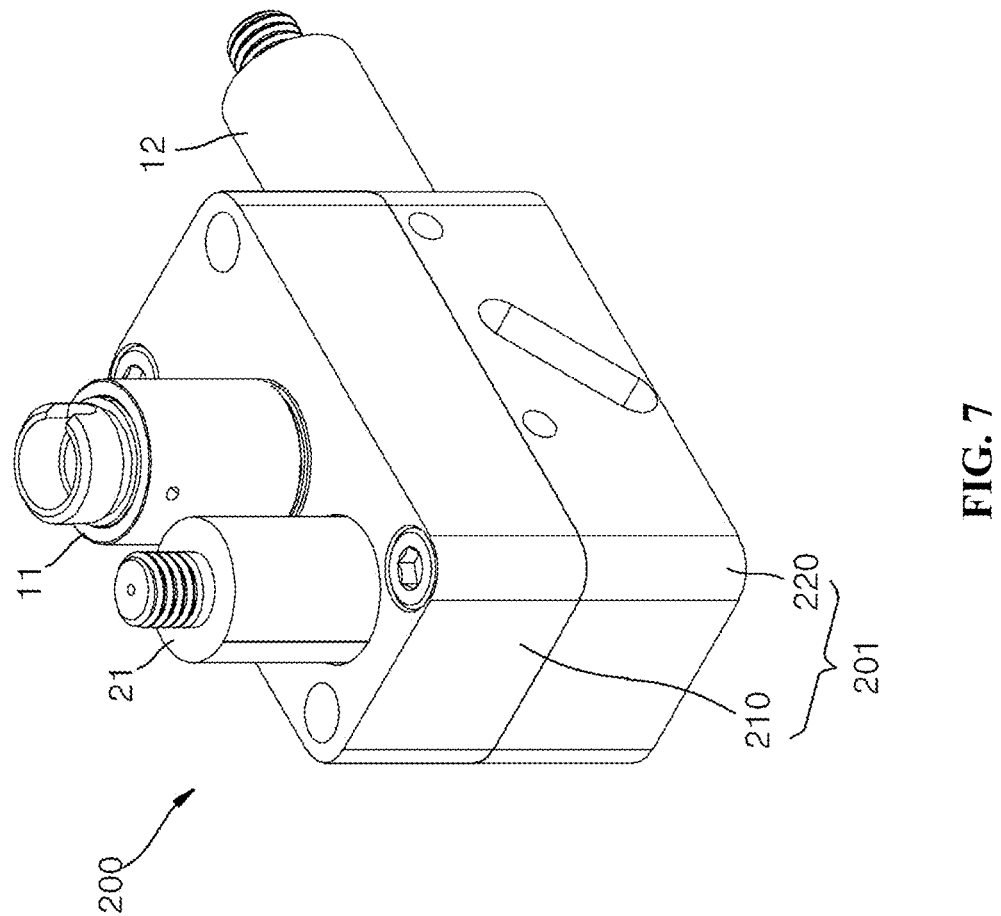
FIG. 7 is a view showing an image acquisition block in which a photoacoustic probe and an ultrasonic probe are integrally installed in the combined photoacoustic/ultrasonic image input apparatus of FIG. 1.

FIG. 7 shows an image acquisition block 200 in which a photoacoustic probe and an ultrasonic probe are integrally installed in the combined photoacoustic/ultrasonic image input apparatus 1.

Referring to the drawing, in the image acquisition block 200, a photoacoustic probe and an ultrasonic probe are installed in a housing 201 including an upper support block 210 and a lower support block 220, and thus, during the scanning operation, the photoacoustic probe and ultrasonic probe may move together. Here, the photoacoustic probe may include a laser probe 11 and a first ultrasonic probe 12, and the ultrasonic probe may include a second ultrasonic probe 21. In this case, during scanning, the laser output unit 11, the first ultrasonic probe 12, and the second ultrasonic probe 21, which are installed in one housing 201, may be transferred together.

The laser probe 11 and the first ultrasonic probe 12, which form the photoacoustic probe, may be staggered at an angle greater than 45 degrees, for example, 90 degrees. When the to-be-examined object 100 is disposed on the lower surface of the image acquisition block 200, the laser probe 11 is disposed vertically, and the laser output passes from top to bottom to reach the to-be-examined object 100. The ultrasonic input generated in the to-be-examined object 100 may be input to the inside of the lower support block 220, and the path thereof is changed through a half mirror disposed therein to then be input to the first ultrasonic probe 12.

The second ultrasonic probe 21 may be staggered at an angle smaller than 45 degrees or substantially parallel to any one of the laser output unit 11 and the first ultrasonic probe 12. In the illustrated embodiment, the second ultrasonic probe 21 may be arranged in parallel with the laser output unit 11.

In this case, the separation distance may be set as much as the horizontal distance between the first position, which is the focusing position of the laser output unit 11, and the second position, which is the focusing position of the second ultrasonic probe 21, and, even when the laser output of the laser output unit 11 and the ultrasonic output of the second ultrasonic probe 21 are simultaneously applied, a photoacoustic image and an ultrasonic image can be simultaneously acquired by the separation distance without interference of the two signals.

As another embodiment, on the upper surface of the housing 201, the first ultrasonic probe 12 and the second ultrasonic probe 21 may be disposed substantially in parallel from the upper surface to the lower surface. In this case, the first ultrasonic probe 12 and the second ultrasonic probe 21 may be placed at right angles to the side of the housing 201 near the first ultrasonic probe 12.

In FIG. 7, the laser probe 11 and the second ultrasonic probe 21 may be arranged so that the first position at which the laser output is focused and the second position at which the ultrasonic output is focused are spaced apart in a first direction and/or a second direction perpendicular to the first direction. In this case, the image acquisition block 200 is fixed to the transfer stage (M/S) of FIG. 4 to perform 2D scanning on a predetermined area.

When scanning of the nth line is completed while the image acquisition block 200 is transferred in the first direction, the image acquisition block 200 is transferred at a set step interval in the second direction and scanning of the (n+1)th line is completed while being transferred in the direction opposite to the first direction, and, when transferred in the second direction by a set distance and number of times, 2D scanning may be completed.

As an embodiment, the image acquisition block 200 may be installed to be spaced apart from the laser probe 11 in the first direction as the second ultrasonic probe 21 on the transfer stage (M/S). In this case, the first position and the second position may be spaced apart by the separation distance in the first direction.

As another embodiment, the image acquisition block 200 may be installed on the transfer stage (M/S) so that the laser probe 11 is spaced apart from the second ultrasonic probe 21 in the second direction. In this case, the first position and the second position may be spaced apart in the second direction. In this case, the first position and the second position may be spaced apart from each other by a separation distance formed by the set number of scan lines in different scan lines.

As an embodiment, for the set laser and ultrasonic output conditions or input conditions, the separation distance may be set in advance by extracting the best image quality (for example, sharpness) of photoacoustic image and ultrasonic image or the shortest distance without deterioration of image quality from information of a plurality of input photoacoustic images and ultrasonic images while varying the separation distance.

As another embodiment, the separation distance may be set in real time as the shortest distance by determining the quality (for example, sharpness) of the photoacoustic images and ultrasonic images from the input photoacoustic image information and ultrasonic image information.

Changing the separation distance may be controlled by horizontally moving or rotating the position of the second ultrasonic probe 21. As an embodiment, the position of the second ultrasonic probe 21 may be controlled to change the separation distance by being horizontally moved. In this case, it may be easy to accurately control the separation distance. As another embodiment, the second ultrasonic probe 21 may be controlled to change the separation distance by being rotated about a reference axis. In this case, the separation distance can be controlled with a small amount of angular adjustment.

As another embodiment, 3D image information for the to-be-examined object may be generated by one-time 2D scanning of the housing, and, within each scanning line, the first ultrasonic input and the second ultrasonic input may be alternately performed with a time difference.

Here, the combined image may be generated by shifting the photoacoustic image information or the ultrasonic image information by a separation distance and combining the same.

As shown in FIG. 1, the combined photoacoustic/ultrasonic image input apparatus 1 may include a photoacoustic input unit 10, an ultrasonic input unit 20, an analog/digital (ND) converter 30, a main controller 40, a trigger controller 50, a pulse signal generator 60, and a linear encoder 70.

The pulse signal generator 60 may generate and output a reference pulse signal at a set interval (e.g., a certain time interval). The linear encoder 70 may include a first linear encoder that generates linear motion information in a first direction and a second linear encoder that generates linear motion information in a second direction that is substantially perpendicular to the first direction. The linear encoder 70 may generate a linear encoder pulse signal corresponding to the first-direction linear motion information of the photoacoustic probe 11, 21.

The laser generator 13 may output a laser pulse at a set interval (e.g., certain positions and/or time intervals) in the to-be-examined object according to the reference pulse signal and the linear encoder pulse signal corresponding to the first-direction linear motion information. As shown in FIG. 5, the laser pulse may be generated such that the linear encoder pulse signal is synchronized with the reference pulse signal after being input.

In this case, since the laser generator 13 outputs the laser pulse according to the linear encoder pulse signal and the reference pulse signal generated by the pulse signal generator 60, the photoacoustic image information corresponding to accurate position information can be generated without a separate scanning trigger.

Meanwhile, the trigger controller 50 may generate an output trigger signal at (e.g., certain positions and/or time intervals) according to the reference pulse signal and the linear encoder pulse signal corresponding to the first-direction linear motion information. As shown in FIGS. 5 and 6, in a corresponding scanning line (n-th scanning line), the first output trigger signal may be used as an ultrasonic start signal, and, after the ultrasonic start signal is input, a preset number of ultrasonic inputs may be made. In this case, as shown in FIG. 5, since the output trigger signal is generated in synchronization with the linear encoder pulse signal and the reference pulse signal, ultrasonic image information according to the ultrasonic input may include ultrasonic image information derived according to accurate position information.

The ultrasonic transceiving unit 22 may generate an ultrasonic output signal corresponding to the output trigger signal, and the ultrasonic probe 21 irradiates the to-be-examined object 100 with an ultrasonic pulse output according to the ultrasonic output signal. Accordingly, an ultrasonic input may be output from the to-be-examined object 100, the ultrasonic input may be received from the ultrasonic transceiving unit 22 through the ultrasonic probe 21, and a digital ultrasonic image signal may be output to the A/D converter 30. The main controller 40 may receive the digital ultrasonic image signal, combine the same with each location information to generate an ultrasonic image, and combine the same with the photoacoustic image generated by being combined with each location information to generate a combined image.

Here, the ultrasonic transceiving unit 22 may generate a photoacoustic image signal and an ultrasonic image signal corresponding to the first-direction linear motion information according to the output trigger signal, respectively, and a combined image of the photoacoustic image signal and the ultrasonic image signal may be generated at the correct position. The ultrasonic transceiving unit 22, including the ultrasonic receiving unit 14 of the photoacoustic input unit 10, may be used as a discrete device.

The ultrasonic probe 21 may output an ultrasonic output corresponding to the output trigger signal generated by the trigger controller 50, and may receive the ultrasonic input corresponding to the first-direction linear motion information according to the output trigger signal.

The main controller 40 may sequentially combine photoacoustic image information corresponding to each trigger pulse of the output trigger signal in a positive or negative direction of the first direction in units of scan lines to generate the photoacoustic image information for the to-be-examined object, may sequentially combine the ultrasonic image information corresponding to each trigger pulse of the output trigger signal in the positive or negative direction of the first direction in units of the same scan line to generate the ultrasonic image information for the to-be-examined object, and may generate a combined image by combining the photoacoustic image information and the ultrasonic image information according to the position information (a linear encoder pulse signal) included in the output trigger signal within the same scan line.

Meanwhile, the linear encoder pulse signal may be a pulse signal output from the linear encoder 70 or a signal corresponding to an integer multiple of the pulse signal.

As an embodiment, after generating photoacoustic image information and ultrasonic image information for one scan line, 2D scanning may also be performed while generating photoacoustic image information and ultrasonic image information for each scan line while moving the photoacoustic probes 11 and 21 in the second direction.

The combined photoacoustic/ultrasonic image input apparatus 1 may include an output selector for selecting a laser pulse output or an ultrasonic output. The output selector may select to output the laser pulse output through the laser probe 11 or the ultrasonic pulse output through the ultrasonic probe 21 according to an output selection signal generated by the main controller 40.

The output selector may be included inside the pulse signal generator 60, and the reference pulse signal may be output to the laser generator 13 or may be output to the trigger controller 50 according to the output selection signal input from the main controller 40.

Here, the main controller 40 may generate and output an output selection signal for the laser output or ultrasonic output, and the pulse signal generator 60 may convert the reference pulse signal according to the output selection signal to the trigger controller 50 for the ultrasonic output or to the laser generator 13 for the laser output, according to the output selection signal.

Meanwhile, the combined photoacoustic/ultrasonic image input apparatus 1 may further include a second linear encoder for generating linear encoder pulse signals corresponding to second-direction linear motion information for the photoacoustic probe 11, 12.

In addition, the combined photoacoustic/ultrasonic image input apparatus 1 may further include a memory for storing plane coordinate values of the photoacoustic probe 11, 21, determined by the first-direction linear motion information and the second-direction linear motion information, photoacoustic image information at the plane coordinate values, and ultrasonic image information for the plane coordinate values of the photoacoustic probe 11, 21 and the to-be-examined object at the plane coordinate values.

The combined photoacoustic/ultrasonic image input apparatus 1 may be implemented by an optical-resolution type combined photoacoustic/ultrasonic image input apparatus 2, which is schematically shown in FIG. 4.

In the combined photoacoustic/ultrasonic image input apparatus 2, the laser pulse generated by the laser generator (L/G) may pass through a half wave plate (HWP), a variable beam splitter/attenuator (VBA), and a fiber coupler (FC), transmitted through a polarization-maintaining single-mode fiber (PM-SMF), and irradiated to the to-be-examined object by a laser probe. Here, the laser probe may include a ferrule coupled to an end of a polarizing fiber, a band pass filter (BPF), first and second objective lenses (OL1 & OL2), and a corrective lens (CL).

Meanwhile, the ultrasonic pulse generated by the ultrasonic transceiver (pulser/receiver (P/R)) may be irradiated to the to-be-examined object through an ultrasonic probe (SFT), and the first ultrasonic input and the second ultrasonic input generated in the to-be-examined object may be input to the ultrasonic transceiver (pulser/receiver (P/R)) through a first ultrasonic probe (SFT) and a second ultrasonic probe (not shown). The ultrasonic image signal input through the ultrasonic transceiver (P/R) may be input to the analog-to-digital converter 30 and a signal processing device (S/P) corresponding to the main controller 40 to generate photoacoustic and ultrasonic image signals. and a combined image may then be generated. The combined image may be displayed on a monitor (DIS) to allow a user to easily identify the displayed combined image.

The laser pulse output and the ultrasonic pulse output may be irradiated to the to-be-examined object through an optical-acoustic beam combiner (OABC), or the first ultrasonic input generated in the to-be-examined object may be input to an ultrasonic probe (SFT) through an optical-acoustic beam combiner (OABC).

The ultrasonic pulse output, the first ultrasonic input, and the second ultrasonic input may output or input by using water contained in the water plate as a medium, and a plastic membrane (PMB) may be disposed on the upper and lower surfaces of the water plate.

Meanwhile, the photoacoustic probe may be transferred in the first direction and/or the second direction by the transfer stage when scanning the to-be-examined object, and the operation of the transfer stage may be controlled by a motion controller (M/C).

Alternatively, in a method for inputting a combined photoacoustic/ultrasonic image, according to an embodiment of the present disclosure, the combined photoacoustic/ultrasonic image may be acquired by using the combined photoacoustic/ultrasonic image input apparatus 1 by the above-described method. Here, in the method for inputting the combined photoacoustic/ultrasonic image, the combined photoacoustic/ultrasonic image may be acquired by the method for generating a combined image by the photoacoustic image signal shown by the timing diagram of FIG. 5 and the method for generating a combined image by the ultrasonic image signal shown by the timing diagram of FIG. 6.

Figure 8:
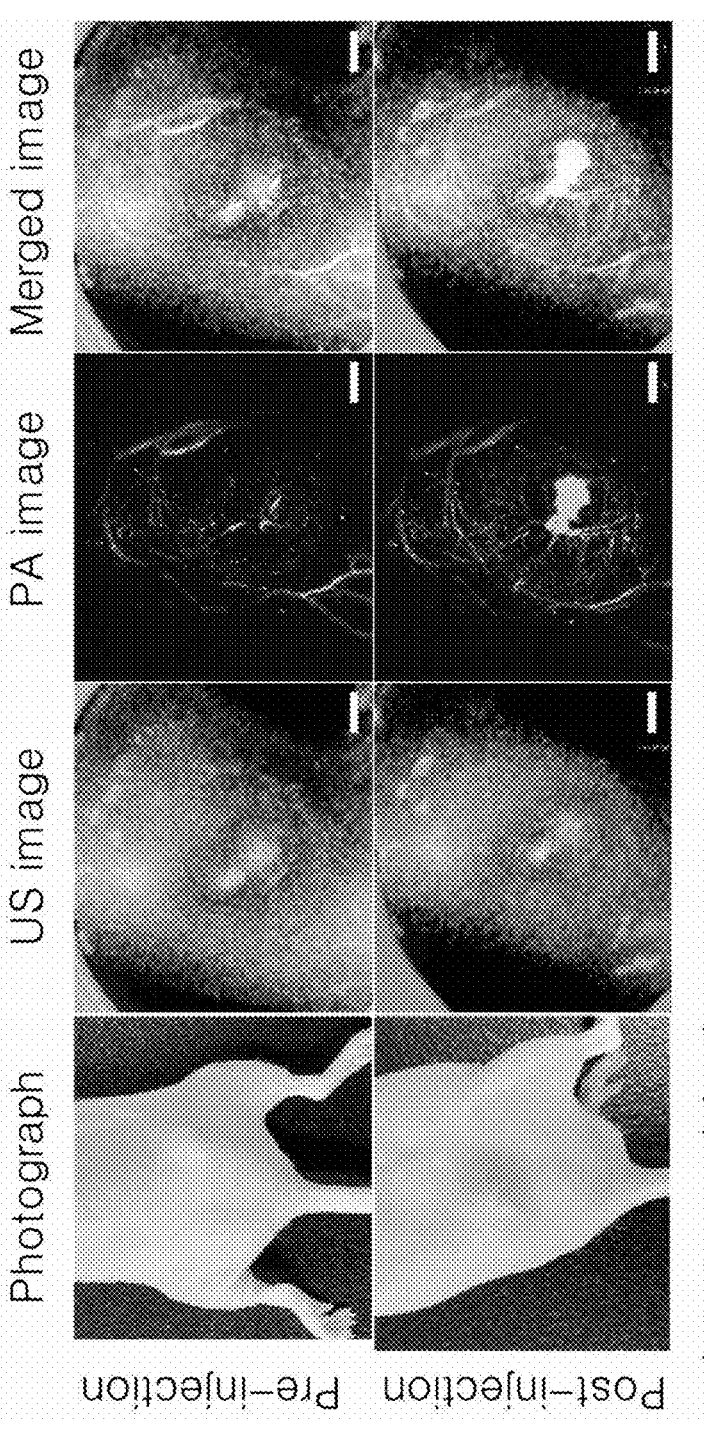
FIG. 8 is a diagram showing examples of images of laboratory rats input and generated by the combined (merged) photoacoustic/ultrasonic image input apparatus of FIG. 1.

FIG. 8 shows examples of images of laboratory mice input and generated by the combined photoacoustic/ultrasonic image input device 1 of FIG. 1.

Referring to the drawing, the upper row shows images before injection of cancer cells into laboratory mice (Pre-injection), and the lower row shows images after injection of cancer cells into laboratory mice (Post-injection). In each case, a photograph of the to-be-examined object and images of an ultrasonic (US) image, a photoacoustic (PA) image), and a combined (merged) image, are shown in order.

In each case, in the ultrasonic (US) image), the structure of the to-be-examined object can be well identified, and in the photoacoustic (PA) image, the image around the blood vessel of the to-be-examined object can be well identified. In the combined image, compared to the photoacoustic (PA) image, which shows only the distribution of blood vessels, the structure is also displayed, and thus, it can be seen that the distribution of blood vessels in a certain part of the to-be-examined object is well represented. This appearance may be displayed on a monitor (DIS) of FIG. 4 so as to be easily identified by a user.

As described above, according to the present disclosure, by generating a photoacoustic image signal and an ultrasonic image signal for the outside and/or inside of the to-be-examined object, respectively, while integrally moving a photoacoustic probe and an ultrasonic probe at high speed, a combined image in which high-resolution photoacoustic and ultrasonic images are combined may be generated by one-time 2D scanning within a short period of time.

In addition, since structure-related information and blood vessel-related information for the inside of a human body are simultaneously displayed in one image, doctors can helped to make a more accurate diagnosis in diagnosing diseases of the inside of the human body.

The technical idea of the present disclosure has been hitherto described through the disclosure of a preferred embodiment of the present disclosure that guarantees the specificity of the idea. A person having ordinary knowledge in the technical field to which the present disclosure belongs will be able to understand that preferred embodiments may be implemented in a modified form within a range that does not deviate from the technical spirit (essential features) of the present disclosure. Therefore, the embodiments disclosed herein should be considered from a descriptive point of view rather than a limiting point of view, and the scope of rights of the present disclosure should be construed as including not only the matters disclosed in the claims but also all differences being within the range equivalent thereto.

What is claimed is:

1. An apparatus for inputting a combined photoacoustic/ultrasonic image, according to an embodiment of the present disclosure, which generates three-dimensional (3D) image information for a to-be-examined object by performing two-dimensional (2D) scanning on the to-be-examined object by a first-direction linear motion of a photoacoustic probe and an ultrasonic probe, and a second-direction linear motion that is perpendicular to the first-direction linear motion, the apparatus comprising:

a transfer unit that linearly moves the photoacoustic probe and the ultrasonic probe with respect to the to-be-examined object in a first direction or a second direction;

a photoacoustic input unit that outputs a laser pulse output to the to-be-examined object, receives a first ultrasound input from the to-be-examined object by the laser pulse output, and generates a photoacoustic image signal;

an ultrasonic input unit that outputs an ultrasonic output to the to-be-examined object, receives a second ultrasonic input from the to-be-examined object by the ultrasonic output, and generates an ultrasonic image signal;

an analog/digital (A/D) converter that receives the photoacoustic image signal and the ultrasonic image signal and converts each into a digital image signal; and a main controller that receives the digital image signal, generates photoacoustic image information and ultrasonic image information for the to-be-examined object, and combines the photoacoustic image information and ultrasonic image information to generate a combined photoacoustic/ultrasonic image;

a pulse signal generator that generates and outputs a reference pulse signal at a set interval;

a linear encoder that generates a linear motion information according to the first-direction linear motion and the second-direction linear motion of the photoacoustic probe and the ultrasonic probe; and a trigger controller that generates an output trigger signal at a set interval based on the reference pulse signal and the linear motion information, wherein the photoacoustic input unit comprises a laser generator that outputs a laser pulse at a set interval to the to-be-examined object based on the reference pulse signal and the linear motion information, wherein a first position at which the laser pulse output is focused and a second position at which the ultrasonic output is focused are spaced apart by a set separation distance.

2. The apparatus as claimed in claim 1, wherein the photoacoustic input unit further comprises a laser probe that outputs the laser pulse output to the to-be-examined object and a first ultrasonic probe that receives the first ultrasonic input, and the ultrasonic input unit comprises a second ultrasonic probe that outputs the ultrasonic output to the to-be-examined object and receives the second ultrasonic input.

3. The apparatus as claimed in claim 2, wherein the laser probe and the first ultrasonic probe are arranged to be staggered at an angle greater than 45 degrees, and the second ultrasonic probe is arranged to be staggered at an angle less than 45 degrees or parallel to either one of the laser probe and the first ultrasonic probe.

4. The apparatus as claimed in claim 2, wherein the laser probe, the first ultrasonic probe, and the second ultrasonic probe are installed in one housing and transferred together.

5. The apparatus as claimed in claim 1, wherein the first position and the second position are spaced apart from each other in the first direction or the second direction.

6. The apparatus as claimed in claim 1, wherein, with respect to the set laser and ultrasonic output conditions or input conditions, the set separation distance is set in advance by extracting the best image quality of the photoacoustic image and the ultrasound image or the shortest distance without image quality degradation from a plurality of pieces of photoacoustic image information and ultrasonic image information input while varying the separation distance.

7. The apparatus as claimed in claim 1, wherein the set separation distance is set in real time as the shortest distance by determining the quality of the photoacoustic image and the ultrasound image from the input photoacoustic image information and the ultrasonic image information.

8. The apparatus as claimed in claim 1, wherein the set separation distance is controlled by moving the second ultrasonic probe that receives the second ultrasonic input rotating about a reference axis.

9. The apparatus as claimed in claim 1, wherein the photoacoustic image information or the ultrasonic image information is shifted by the set separation distance and combined.

10. The apparatus as claimed in claim 1, wherein the ultrasonic input comprises an ultrasonic transceiving unit that generates an ultrasonic output signal (output channel) for generating the ultrasonic output, receives the first ultrasonic input and the second ultrasonic input, and generates a photoacoustic image signal and an ultrasonic image signal, respectively, the ultrasonic transceiving unit includes a first input channel and a second input channel, the photoacoustic image signal may be generated by inputting the first ultrasound input to the first input channel, and the ultrasound image signal may be generated by inputting the second ultrasound input to the second input channel.

11. The apparatus as claimed in claim 10,
wherein the ultrasonic transceiving unit generates the photoacoustic image signal and the ultrasonic image signal corresponding to a linear motion information according to the first-direction linear motion of the photoacoustic probe and the ultrasonic probe, respectively, according to an output trigger signal which is generated by a trigger controller based on a reference pulse signal and the linear motion information.

12. The apparatus as claimed in claim 2, wherein the second ultrasonic probe outputs an ultrasonic output corresponding to an output trigger signal generated by a trigger controller and receives the ultrasonic input corresponding to the linear motion information according to the output trigger signal.

13. The apparatus as claimed in claim 1, wherein, in the main controller: photoacoustic image information for the to-be-examined object is generated by sequentially combining the photoacoustic digital image signal with the photoacoustic image information corresponding to each trigger pulse of the output trigger signal in the positive or negative direction of the first direction in units of scan lines; and ultrasonic image information for the to-be-examined object is generated by sequentially combining the ultrasonic digital image signal with the ultrasonic image information corresponding to each trigger pulse of the output trigger signal in the positive or negative direction of the first direction in units of scan lines.

14. The apparatus as claimed in claim 1, wherein the laser pulse output and the ultrasonic output are simultaneously output.

15. The apparatus as claimed in claim 1, wherein the reference pulse signal is output to the trigger controller and the laser generator.

16. The apparatus as claimed in claim 4, wherein a 3D image information for the to-be-examined object is generated by performing 2D scanning on the to-be-examined object by the housing which includes the laser probe, the first ultrasonic probe and the second ultrasonic probe, and, within each scanning line, the first ultrasonic input and the second ultrasonic input are alternately performed.

17. The apparatus as claimed in claim 4, further comprising:
a memory for storing plane coordinate values of the photoacoustic probe, determined by the linear motion information, photoacoustic image information at the plane coordinate values, and ultrasonic image information for the plane coordinate values of the photoacoustic probe and the to-be-examined object at the plane coordinate values.

* * * * *